United States Patent [19]

Teach

[11] 4,138,495
[45] Feb. 6, 1979

[54] N-SUBSTITUTED PYRROLIDONES AND THEIR USE AS MITICIDES

[75] Inventor: Eugene G. Teach, El Cerrito, Calif.

[73] Assignee: Stauffer Chemical Company, Westport, Conn.

[21] Appl. No.: 907,514

[22] Filed: May 19, 1978

[51] Int. Cl.$^2$ .................. A01N 9/12; A01N 9/22; C07D 207/26
[52] U.S. Cl. .................. 424/274; 260/326.5 S; 260/326.5 J
[58] Field of Search .................. 260/326.5 S; 424/274

[56] References Cited

U.S. PATENT DOCUMENTS

| | | | |
|---|---|---|---|
| 3,956,313 | 5/1976 | Freyermuth et al. | 260/326.5 S |
| 4,069,038 | 1/1978 | Teach | 260/326.5 S |

FOREIGN PATENT DOCUMENTS

1361388  7/1974  United Kingdom .............. 260/326.5 S

*Primary Examiner*—Nicholas S. Rizzo
*Assistant Examiner*—James H. Turnipseed
*Attorney, Agent, or Firm*—M. Henry Heines

[57] ABSTRACT

Compounds having the formula $$R^1-S-CH-\underset{R^2-CH-CH_2}{\overset{\overset{O}{\underset{\|}{C}}}{\diagdown}} N-R^3$$

in which
$R^1$ is $C_1-C_4$ alkyl,
$R^2$ is selected from the group consisting of hydrogen and $-CH_2X$ in which X is halogen, and
$R^3$ is selected from the group consisting of allyl and

[benzene ring structure with Y substituent]

in which Y is selected from the group consisting of halogen and trifluoromethyl and their use as miticides are disclosed herein.

21 Claims, No Drawings

N-SUBSTITUTED PYRROLIDONES AND THEIR USE AS MITICIDES

BRIEF DESCRIPTION OF THE INVENTION

This invention relates to miticidal compounds, compositions and methods of use.

The compounds of the present invention have the following general formula

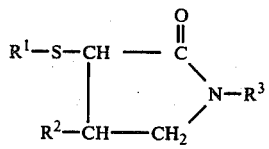

in which
$R^1$ is $C_1$-$C_4$ alkyl,
$R^2$ is selected from the group consisting of hydrogen and —$CH_2X$ in which X is halogen, and
$R^3$ is selected from the group consisting of allyl and

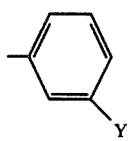

in which Y is selected from the group consisting of halogen and trifluoromethyl.

Within the scope of the above formula, certain embodiments are preferred. In one such embodiment, $R^1$ is selected from the group consisting of methyl and ethyl, $R^2$ is selected from the group consisting of hydrogen and chloromethyl, and Y is selected from the group consisting of chlorine and trifluoromethyl. Other preferred embodiments will be apparent from the following description. All carbon atom ranges disclosed herein are intended to be inclusive of their upper and lower limits.

The compounds of the present invention, either alone or in combination with an inert diluent carrier, are useful as insecticides, particularly in the control of mites, when used in an insecticially or miticidally effective amount.

By "insecticidally effective amount" or "miticidally effective amount" is meant the amount of the herein disclosed compounds which then applied in any conventional manner to the habitat of insects or mites, their feedstuffs, or the insects or mites themselves, will kill or substantially injure a significant portion thereof. The compounds are particularly effective when applied directly to mites, especially to mites in the embryonic stage of their development.

The term "halogen" is used herein to designate a member selected from the group consisting of fluorine, chlorine, bromine, and iodine.

DETAILED DESCRIPTION OF THE INVENTION

The compounds of the present invention can be prepared by a variety of techniques.

For compounds where $R^2$ is —$CH_2X$, one such technique involves the acylation of a primary amine followed by treatment of the resulting amide with a 2-alkenyl halide, both reagents appropriately substituted to give the desired final product, and both reactions occurring in the presence of a base, for example:

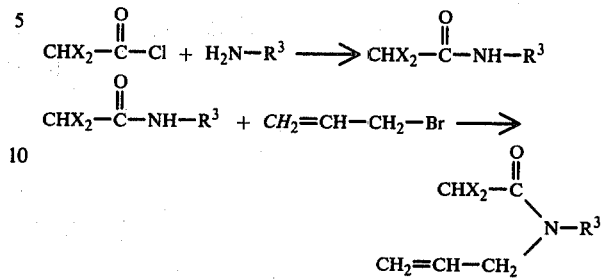

The above product is then cyclized with a ferrous ion or other transition-metal-containing catalyst to form a 3-halopyrrolidone. Finally, the latter is reacted with a sodium alkyl mercaptide to yield the desired 3-alkylthiopyrrolidone.

Alternatively, an allyl amine can be reacted with a dihaloacetyl chloride as follows:

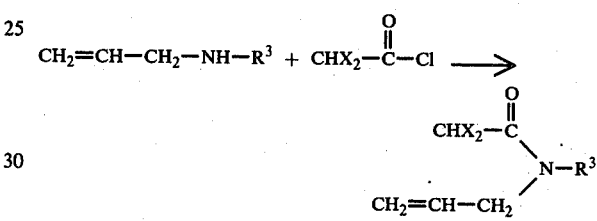

This is again followed by the cyclization reaction and the mercaptide substitution.

These and similar techniques are described in U.S. Pat. No. 4,069,038, issued Jan. 13, 1978, and commonly assigned U.S. Pat. application Ser. No 864,021, filed Dec. 23, 1977. Both of these references are incorporated herein by reference.

For compounds where $R^2$ is hydrogen, the appropriately substituted amine can be reacted with butyrolactone, followed by bromination and subsequent substitution by an alkyl mercaptide, for example:

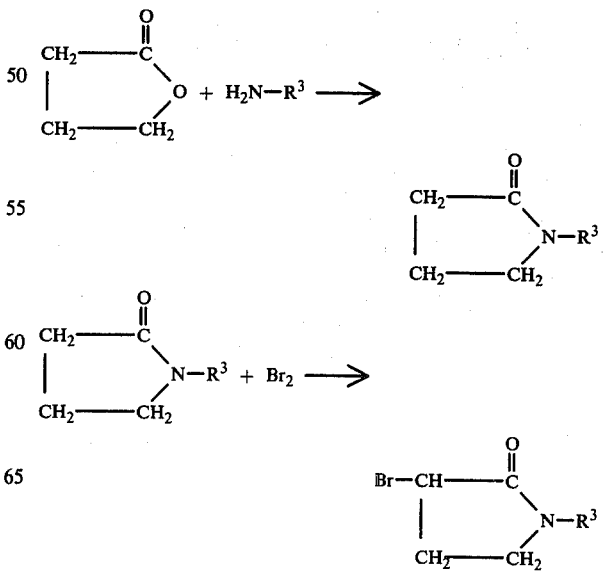

-continued

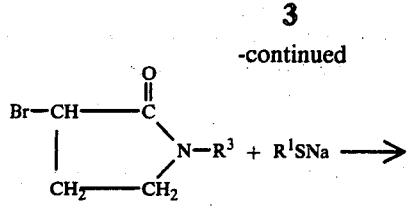

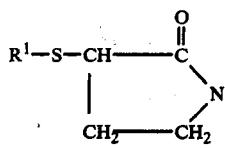

Primary amines capable of use in the above preparations are, in most cases, commercially available, but can be prepared in any event by methods well documented in the chemical literature. Such documentation can be found in Wagner and Zook, "Synthetic Organic Chemistry," John Wiley and Sons, New York (1961), Chapter 24.

The following examples are offered to illustrate the preparation of the compounds of the present invention, and are not intended to place any limitations on the scope of the invention.

EXAMPLE 1

N-Allyl-3-methylthio-4-chloromethyl-2-pyrrolidone

N-allyl-3-chloro-4-chloromethyl-2-pyrrolidone was prepared by the procedure described in Example 1 of U.S. Pat. No. 4,069,038. Sodium methyl mercaptide was then prepared by adding 43.2 grams (g) of a 25% methanol solution of sodium methoxide to 100 milliliters (ml) of dimethylformamide, and bubbling in methyl mercaptan until the latter was no longer absorped by the solution (amounting to approximately 10 g of the mercaptan). The resulting sodium methyl mercaptide was then added dropwise to 20.8 g (0.1 mole) of pyrrolidone over a period of one hour, with the temperature maintained at 0° C. The mixture was then stirred overnight at room temperature. The product was then filtered, stripped of solvent, and extracted with ether to yield 17.4 g (79% yield) of the title compound, with structure confirmed by nuclear magnetic resonance (NMR) analysis, and with refractive index ($n_D^{30}$) of 1.5238. This compound is shown in Table I below as Compound No. 1.

EXAMPLE 2

N-(m-Trifluoromethylphenyl)-3-methylthio-4-chloromethyl-2pyrrolidone

In the same manner as descried above for Example 1, sodium methyl mercaptide prepared from 6.5 g of a 25% methanol solution of sodium methoxide in 50 ml of dimethylformamide was added to 9.4 g (0.034 mole) of N-(m-trifluoromethylphenyl)-3-chloro-4-chloromethyl-2-pyrrolidone (prepared according to the procedure described in U.S. Pat. No. 4,069,038). The product weighed 9.3 g, representing 85% yield based on the pyrrolidone, structure confirmed by NMR analysis, with refractive index $n_D^{30} = 1.5028$. This compound is shown in Table I as Compound No. 2.

EXAMPLE 3

N-(m-Trifluoromethylphenyl)-3-methylthio-2-pyrrolidone

A reaction flask was charged with 70.0 g (0.434 mole) of m-trifluoromethylaniline and 37.4 g (0.434 mole) of butyrolactone. The mixture was heated to reflux at 198° C for 185 minutes. Then, 1.0 g (0.0058 mole) of ptoluenesulphonic acid was added, and the resulting mixture was refluxed for an additional 100 minutes, during which time the temperature dropped from 164° C to 138° C. The mixture was then cooled, a DEan-Stark trap was installed on the condenser, and 50 ml of mesitylene was added. The mixture was then refluxed at 181-187° C until water was no longer produced. The precipitate formed by the reaction was filtered out of the mixture and dried in vacuo, yielding 45.6 g of 1-(m-trifluoromethylphenyl)-2-pyrrolidone, melting point 65°-66° C.

Of this material, 30 g (0.131 mole) was charged to a reaction flask together with 2 ml (3.15 g, 0.0229 mole) of phosphorus trichloride and 130 ml of chlorobenzene. The flask was then heated to 105° C and 6.70 ml (20.9 g, 0.131 mole) of bromine was added through a dropping funnel over a period of 80 minutes, while the evolving hydrogen bromide gas was removed by a nitrogen purge. The reaction mixture was heated for an additional 55 minutes, then cooled, washed with a 5% aqueous sodium thiosulfate solution, dried over magnesium sulfate, filtered, and stripped of solvent. The solution was then diluted with methanol and cooled overnight in a refrigerator. The crystals which were thus formed yielded 17.2 g of 1-(m-trifluoromethylphenyl)-3-bromo-2-pyrrolidone, melting point 79-83° C.

A flask was charged with 5.0 g (0.0162 mole) of the above material and 15.9 ml of sodium methyl mercaptide in ethanol (amounting to 0.0178 mole of the mercaptide). The mixture was heated to reflux for two hours, then cooled. A white precipitate formed. To the mixture was added 50 ml each of methylene chloride and water. The layers were then separated, and the organic layer was washed with 2N caustic solution followed by water, then dried over magnesium sulfate, filtered, and stripped. The resulting product consisted of 3.7 g of a clear liquid. The structure was confirmed as that of the title compound by mass spectroscopy and NMR analyses, representing a yield of 95% based on the 1-(m-trifluoromethylphenyl)-3-bromo-2-pyrrolidone, with refractive index $n_D^{30} = 1.5365$. This compound is shown in Table I as Compound No. 5.

These and other compounds analogously prepared are listed in Table I as representative examples of compounds within the scope of the present invention. Miticide test procedures and results obtained using the compounds of Table I are shown following the table.

Table I

Compounds and Physical Properties $$R^1-S-CH-\overset{\displaystyle O}{\underset{\displaystyle |}{C}}\diagdown$$
$$\qquad\qquad\qquad\qquad N-R^3$$
$$R^2-CH-CH_2\diagup$$

| Compound No. | $R^1$ | $R^2$ | $R^3$ | $n_D^{30}$ Refractive Index |
|---|---|---|---|---|
| 1 | —CH₃ | —CH₂Cl | —CH₂CH=CH₂ | 1.5238 |
| 2 | —CH₃ | —CH₂Cl | ⟨phenyl-3-CF₃⟩ | 1.5028 |
| 3 | —CH₃ | —CH₂Cl | ⟨phenyl-3-Cl⟩ | 1.5828 |
| 4 | —CH₂CH₃ | —CH₂Cl | ⟨phenyl-3-CF₃⟩ | 1.5155 |
| 5 | —CH₃ | —H | ⟨phenyl-3-CF₃⟩ | 1.5365 |

Miticide Test Procedures

Post-embryonic Mites

A pinto bean plant (Phaseolus sp.), approximately 10 centimeters (cm) tall was transplanted into sandy loam soil in a 3-inch clay pot and infested with two-spotted mites [*Tetranychus urticae* (Koch)] of mixed ages and sexes. Twenty-four hours later the infestd plants were inverted and dipped for 2–3 seconds in a 50/50 acetone/water solution of the test compound. The treated plant was held in a greenhouse for seven days. Mortality was then determined for the adult mites.

Mite Eggs

The procedure used for mite eggs was the same as that used for the post-embryonic mites, with the exception that the pinto bean plants were first dipped in a 50/50 acetone/water solution containing 0.05% by weight of 2-methoxycarbonyl-1-methylvinyl dimethyl phosphate, α-isomer (a commercial insecticide, also known as "PHOSDRIN ®" or "mevinphos", available from Shell Chemical Company). The latter is effective in killing most post-embryonic forms of the mites at this concentration without harming the eggs. The leaves were then allowed to dry and were subsequently treated with a test compound solution as described above in the post-embryonic test description. Seven days later, the plants were examined for the presence of immature mites, and mortality was determined.

Tahle II is a summary of the results of the above tests performed on the compounds of Table I. These test results are expressed as $LD_{50}$ values, which represent the dose of test compound which was lethal to 50% of either the adult or egg population in the test. The entries in Table II were obtained as follows:

In each test, the initial test compound solution contained 0.05% by weight of the test compound. Those compounds showing less than 50% kill at this level are represented in the table by the figure "0.05%" preceded by a "greater than" sign (>). Those compounds showing approximately 50% kill are represented by the figure "0.05%" alone. Those compounds showing greater than 50% kill were subjected to further testing at successively lower levels, until the level was found at which approximately 50% kill was achieved. The latter level is listed as the $LD_{50}$ for this group.

The primary screening level of 0.05% was selected for purposes of convenience only, and is not intended to be understood as representing the highest level at which a viable test for miticidal activity can be conducted. Dashes are used in Table II where no tests were performed at all.

TABLE II

Miticidal Activity - Approximate $LD_{50}$ Values (Weight % in Test Solution)

| Compound Number | Post-embryonic Mites | Mite Eggs |
|---|---|---|
| 1 | >.05 | .05 |
| 2 | .05 | .006[a] |
| 3 | >.05 | .03 |
| 4 | —[b] | .008 |
| 5 | .05 | — |

[a] Average of two trials.
[b] Host plant died.

The compounds of this invention are generally used in formulations suitable for convenient application. In general, such formulations will contain inert of occasionally active ingredients or diluent carriers in addition to the active compound. Examples of such ingredients or carriers are organic solvents, such as sesame oil, xylene range solvents; and heavy petroleum; water; emulsifying agents; surface active agents; talc; pyrophyllite; diatomite; gypsum; clays; and propellants, such as dichlorodifluoromethane.

The active compounds can further be combined with dust carriers for application as dusts, with granular carriers for application by fertilizer spreaders or ground or airplane seeders, with wettable powders or flowable carriers for application as water suspensions, or with solvents and surface active materials for application as sprays, aerosols, or emulsions. The compounds or their formulated mixtures can be applied to any habitat of pests. Examples of such habitats are insect dwellings, clothing, plant surfaces, domestic animals, and soil. If desired, however, the active composition can be applied directly to organic matter, seeds or feedstuffs in general, upon which the pests feed, or directly to the pests themselves. When applied in such a manner, it will be advantageous to use a formulation which is not volatile.

The amount of active compound or formulation which is considered to be insecticidally effective is that amount which, when applied to the pest habitat or feedstuff, will kill or substantially injure a significant portion thereof. The active compounds of this invention can be employed either as the sole pesticide component of the formulations or as one of a mixture of compounds in the formulation having similar utility. Furthermore, the presently disclosed pesticide compositions need not be active as such. The purposes of this invention will be fully served by a composition which is rendered active by external influences, such as light, or by physiological action occurring when the preparation is ingested or penetrates into the body of the pest.

The precise manner in which the pesticide compounds of this invention are used in any particular instance will be readily apparent to a person skilled in the art. Generally, the active pesticidal compound will be used as a component of a liquid composition; for example, an emulsion, suspension, or aerosol spray. While the concentration of the active pesticide compound in the present formulation can vary within rather wide limits, ordinarily, the compound will comprise from about 0.01% to about 50.0% by weight of the formulation.

What is claimed is:

1. A compound having the formula

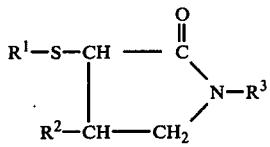

in which
R$^1$ is C$_1$-C$_4$ alkyl,
R$^2$ is selected from the group consisting of hydrogen and -CH$_2$X in which X is halogen, and
R$^3$ is selected from the group consisting of allyl and

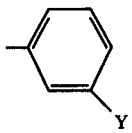

in which Y is selected from the group consisting of halogen and trifluoromethyl.

2. A compound according to claim 1 in which R$^1$ is selected from the group consisting of methyl and ethyl, R$^2$ is selected from the group consisting of hydrogen and —CH$_2$Cl, and Y is selected from the group consisting of chlorine and trifluoromethyl.

3. A compound according to claim 1 in which R$^1$ is methyl, R$^2$ is chloromethyl, and R$^3$ is allyl.

4. A compound according to claim 1 in which R$^1$ is methyl, R$^2$ is chloromethyl, and R$^3$ is m-trifluoromethylphenyl.

5. A compound according to claim 1 in which R$^1$ is methyl, R$^2$ is chloromethyl, and R$^3$ is m-chlorophenyl.

6. A compound according to claim 1 in which R$^1$ is ethyl, R$^2$ is chloromethyl, and R$^3$ is m-trifluoromethylphenyl.

7. A compound according to claim 1 in which R$^1$ is methyl, R$^2$ is hydrogen, and R$^3$ is m-trifluoromethylphenyl.

8. A miticidal composition comprising
a. a compound having the formula

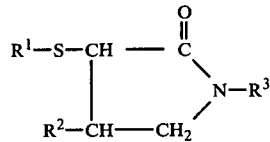

in which
R$^1$ is C$_1$-C$_4$ alkyl,
R$^2$ is selected from the group consisting of hydrogen and —CH$_2$X is halogen, and
R$^3$ is selected from the group consisting of allyl and

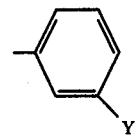

in which Y is selected from the group consisting of halogen and trifluoromethyl; and
b. an inert diluent carrier.

9. A composition according to claim 8 in which R$^1$ is selected from the group consisting of methyl and ethyl, R$^2$ is selected from the group consisting of hydrogen and -CH$_2$Cl, and Y is selected from the group consisting of chlorine and trifluoromethyl.

10. A composition according to claim 8 in which R$^1$ is methyl, R$^2$ is chloromethyl, and R$^3$ is allyl.

11. A composition according to claim 8 in which R$^1$ is methyl, R$^2$ is chloromethyl, and R$^3$ is m-trifluoromethylphenyl.

12. A composition according to claim 8 in which R$^1$ is methyl, R$^2$ is chloromethyl, and R$^3$ is m-chlorophenyl.

13. A composition according to claim 8 in which R$^1$ is ethyl, R$^2$ is chloromethyl, and R$^3$ is m-trifluoromethylphenyl.

14. A composition according to claim 8 in which R$^1$ is methyl, R$^2$ is hydrogen, and R$^3$ is m-trifluoromethylphenyl.

15. A method of controlling mites comprising applying to said mites a miticidally effective amount of a compound having the formula

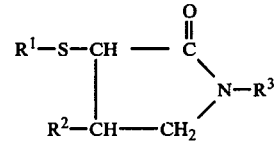

in which
R$^1$ is C$_1$-C$_4$ alkyl,
R$^2$ is selected from the group consisting of hydrogen and —CH$_2$X in which X is halogen, and
R$^3$ is selected from the group consisting of allyl and

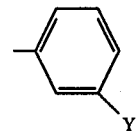

in which Y is selected from the group consisting of halogen and trifluoromethyl.

16. A method according to claim 15 in which R$^1$ is selected from the group consisting of methyl and ethyl, R$^2$ is selected from the group consisting of hydrogen and —CH$_2$Cl, and Y is selected from the group consisting of chlorine and trifluoromethyl.

17. A method according to claim 15 in which R$^1$ is methyl, R$^2$ is chloromethyl, and R$^3$ is allyl.

18. A method according to claim 15 in which R$^1$ is methyl, R$^2$ is chloromethyl, and R$^3$ is m-trifluoromethylphenyl.

19. A method according to claim 15 in which R$^1$ is methyl, R$^2$ is chloromethyl, and R$^3$ is m-chlorophenyl.

20. A method according to claim 15 in which R$^1$ is ethyl, R$^2$ is chloromethyl, and R$^3$ is m-trifluoromethylphenyl.

21. A method according to claim 15 in which R$^1$ is methyl, R$^2$ is hydrogen, and R$^3$ is m-trifluoromethylphenyl.

* * * * *